United States Patent [19]

Burch et al.

[11] Patent Number: 4,846,584
[45] Date of Patent: Jul. 11, 1989

[54] AUTOMATED CALORIMETER AND METHODS OF OPERATING THE SAME

[75] Inventors: Robert H. Burch, Tonawanda; Joseph M. Gravelle, Amherst, both of N.Y.

[73] Assignee: Pennwalt Corporation, Philadelphia, Pa.

[21] Appl. No.: 134,392

[22] Filed: Dec. 17, 1987

[51] Int. Cl.[4] ............................................. G01K 17/00
[52] U.S. Cl. ....................................... 374/31; 422/198
[58] Field of Search ............................ 374/31, 40, 41

[56] References Cited

U.S. PATENT DOCUMENTS

| | | | |
|---|---|---|---|
| 2,163,730 | 6/1939 | Goetzl | 374/40 |
| 3,631,717 | 1/1972 | Kato et al. | 374/40 |
| 3,888,726 | 6/1975 | Hultman | 436/147 X |
| 3,994,164 | 11/1976 | Regenass et al. | 374/31 |
| 4,073,182 | 2/1978 | Allington | 436/147 |
| 4,456,389 | 6/1984 | Regenass et al. | 374/31 |

FOREIGN PATENT DOCUMENTS 455325  4/1968  Switzerland .

Primary Examiner—Daniel M. Yasich
Attorney, Agent, or Firm—Panitch Schwarze Jacobs & Nadel

[57] ABSTRACT

A fast reacting, automated calorimeter includes a reaction vessel containing a chemically reacting mass, a fluid circulation system containing heat transfer fluid, a portion of the system passing the fluid through the reaction vessel for exchanging heat between the fluid and the reacting mass, a flow rate controller at least generally responsive to variations in temperature of the reacting mass to vary the flow rate of the fluid circulated through the reaction vessel portion of the circulation system, a flow rate signal generator generating a signal related to the varying flow rate of the fluid passing through the reaction vessel portion of the fluid circulation, and a circuit, preferably including a computer, responsive at least to the flow rate signal and generating a heat flow signal generally related to instantaneous rate of heat exchange between the reacting mass and the fluid. Heat tranfer is measured and the reaction is controlled by varying, during the course of the reaction, the flow rate of heat transfer fluid fed into the reaction vessel at a predetermined temperature.

20 Claims, 2 Drawing Sheets

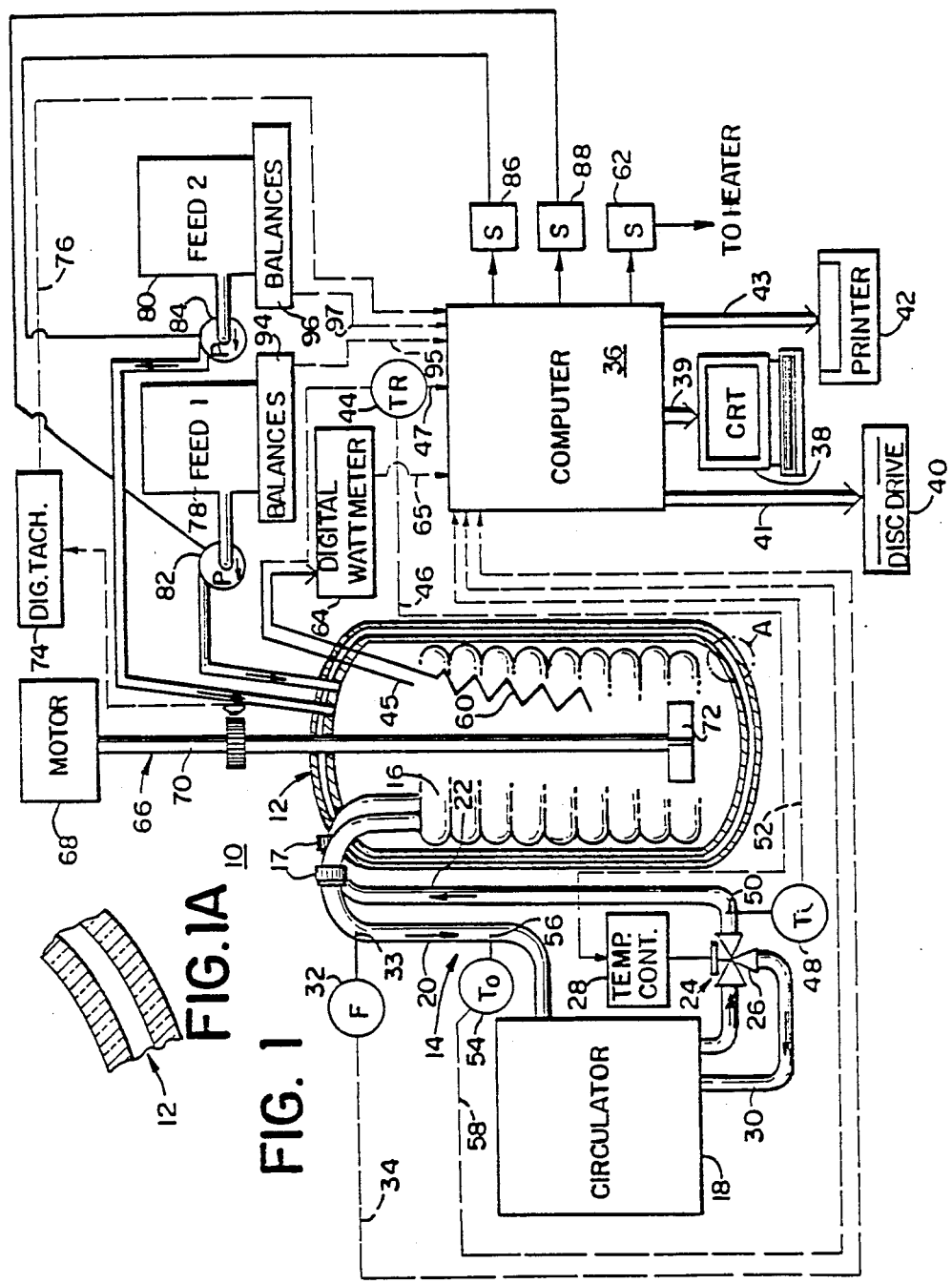

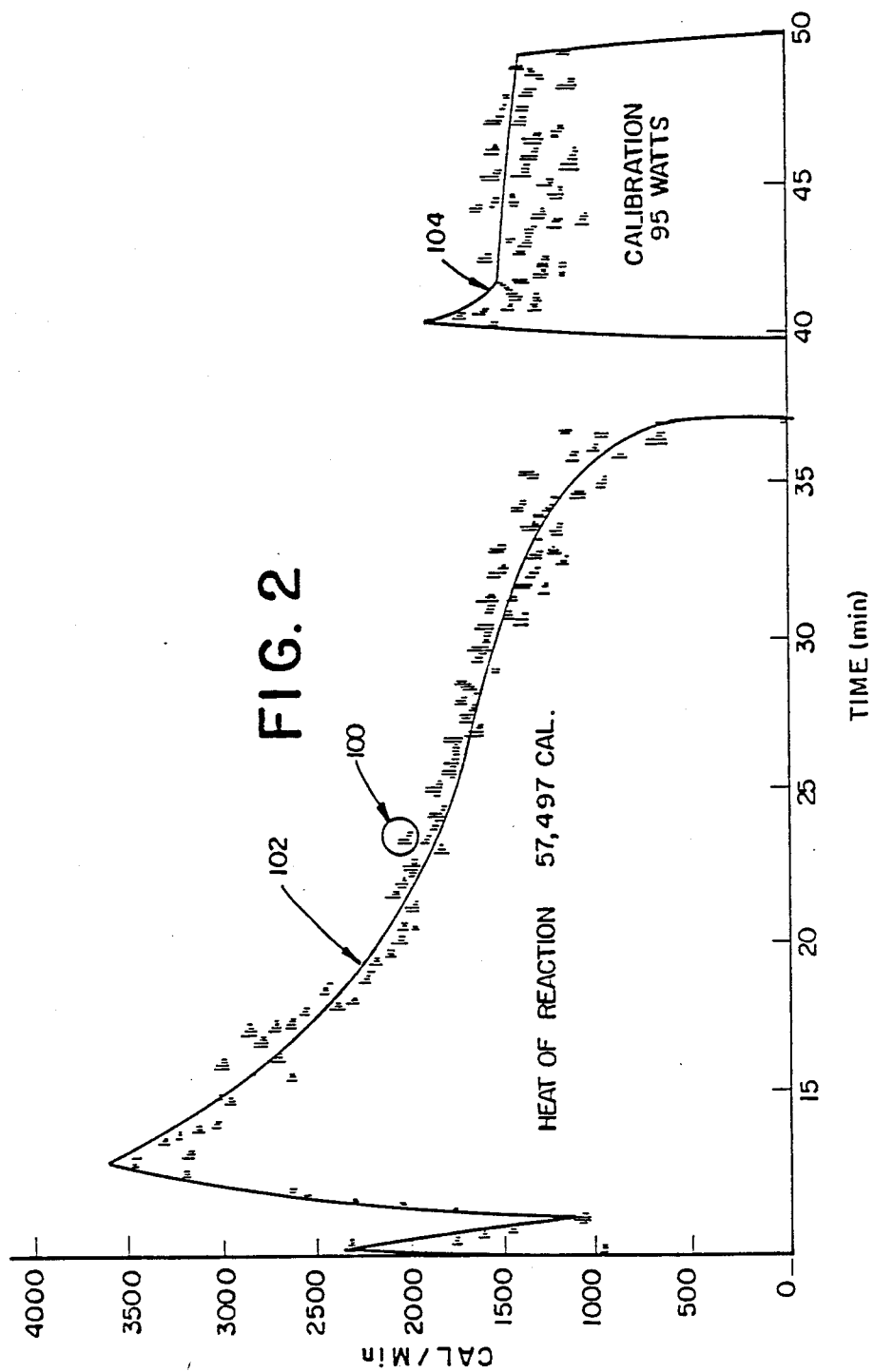

AUTOMATED CALORIMETER AND METHODS OF OPERATING THE SAME

FIELD OF THE INVENTION

The invention relates to calorimeters for determining the heat of reaction of a chemically reacting mass and, in particular, to automated calorimeters providing automatic reaction control and heat transfer measurement and to their methods of operation.

BACKGROUND OF THE INVENTION

Calorimeters are devices for measuring the heat absorbed or released by a chemical reaction. Automated devices available today perform appropriate measurements and utilize those measurements to determine automatically instantaneous rates of heat exchange. These rates can be summed or integrated to provide a net or effective heat of reaction.

Swiss Patent No. 455,320 discloses an automatic calorimeter in which a heat transfer fluid is circulated at a constant flow rate through the interior of a reaction vessel by means of a coil. The temperature of the liquid is varied in response to the difference between a predetermined set-point temperature and an interior temperature of the reaction vessel. The temperature variation of the fluid is several times greater than the actual deviation between set point and sensed reaction vessel temperatures to anticipate the delay in the response of the system. The remainder of the heat transfer fluid circulation system is essentially closed and includes a heating and/or cooling device in a loop with the reaction vessel. Fluid passing through the coil is returned to the heating/cooling device and its temperature is adjusted in response to the difference between the set point temperature and the reaction temperature.

U.S. Pat. Nos. 3,994,164 and 4,456,389 disclose successive improvements to the device of Swiss Patent No. 455,325. The devices of the two U.S. patents differ from that of the Swiss Patent by incorporating simultaneously operating heating and cooling systems and controllers which vary the outputs of the two systems to vary the temperature of the fluid entering the reaction vessel. Additionally, each of the reaction vessels includes a mantle or jacket surrounding an inner shell containing the reaction mass for circulating fluid around the shell rather than through a coil within the shell.

One of the major drawbacks of the prior art calorimeter devices referred to above is that they require potentially widely diverging temperature swings of the heat transfer fluid. Since heat transfer characteristics (i.e. specific heat) of the fluid vary with temperature, more error is introduced by increasing the temperature range to which the heat transfer fluid is subjected.

Another significant drawback of the Swiss device is that system response to unanticipated rapid exothermic or endothermic reactions would be slow because of thermal inertia of the heat exchange fluid. It would be difficult to quickly cool down or heat up the heat transfer fluid, the heating device reservoir and piping to maintain or rapidly bring the reaction under control. Failure to respond quickly to a reaction exotherm could result in a runaway reaction and possible explosion.

The calorimeter devices of U.S. Pat. Nos. 3,994,164 and 4,456,389 provide two reservoirs for more rapid response. However, these devices circulate the heat transfer fluid through a jacket surrounding the reaction chamber shell. Jacketed vessels have a more limited heat transfer surface than can be achieved with a coil immersed in the reaction mass. Reaction vessels are typically made of glass which is a poor heat transmitter. These factors can lead to drift of the reaction vessel interior temperature from the desired set point, ultimately resulting in inconsistent results and/or runaway reactions.

Moreover, in such jacketed systems, when the temperature of the reaction mass approaches that of the jacket, a large degree of error can be introduced when measuring a heat of reaction if the jacket temperature varies significantly from ambient temperature. This is due to heat transfer between the jacket and surrounding atmosphere.

Lastly, conducting the heat transfer fluid through a jacket surrounding the sides of the reaction vessel will obscure the only good view an operator may have of the reacting mass, even if a glass walled vessel is employed.

The method of operation of all of these prior art devices tends to magnify certain system errors. As is pointed out in the Swiss patent, heat transfer is related to the temperature difference ($\Delta T$) between the heat exchanger inlet and outlet temperatures. As U.S. Pat. No. 3,994,164 points out, the system is operated so as to keep the temperature difference between the heat exchanger inlet and outlet to less than one degree Centigrade. These temperatures are measured by instruments which have a limited accuracy. As the temperature difference being measured becomes smaller, the percentage contribution of instrumentation erro to the measurement becomes greater.

It would be beneficial to provide a calorimeter and method of operating such device which rapidly responds to reaction mass temperature variations.

It further would be beneficial to provide a calorimeter and method of operating such device in which the temperature excursions of the heat transfer fluid are kept to a minimum to minimize any errors introduced due to variations in the specific heat of fluid.

It further would be beneficial to provide a calorimeter and method of operating such device in which temperature differences between the heat transfer fluid inlet and outlet from the reaction vessel are significantly more than one degree Centigrade to minimize the contribution of temperature measurement errors in the determination of heat transfer.

SUMMARY OF THE INVENTION

The aforesaid benefits and others are provided by a calorimeter for determining heat of reaction of a chemically reacting mass comprising reaction vessel means for containing the chemically reacting mass; a fluid circulation system containing a heat transfer fluid, a portion of the system passing the fluid through the reaction vessel means for exchanging heat between the fluid and the reacting mass; flow rate control means at least generally responsive to variations in temperature of the reacting mass for varying flow rate of the fluid circulated through the reactor vessel portion of the circulation system; flow rate signal means for generating a signal related to varying flow rate of the fluid passing through the reaction vessel portion of the fluid circulation system; and circuit means responsive at least to the flow rate signal for generating a heat flow signal generally related to instantaneous rate of heat exchange between the reacting mass and the fluid.

The invention further includes a method for determining the heat of reaction of a reacting mass utilizing a reaction vessel and a heat transfer fluid comprising the generally simultaneous steps of: chemically reacting the mass within the reaction vessel; circulating the fluid through a fluid circulation system, a portion of the system passing the fluid through the reaction vessel for exchanging heat between the fluid and the reacting mass; varying flow rate of the fluid passing through the reaction vessel portion of the circulation system at least generally in response to variations in temperature of the reacting mass; generating a signal related to varying flow rate of the fluid passing through the reaction vessel portion of the circulation system; and generating a heat flow signal generally related to instantaneous rate of heat exchange between the reacting mass and the fluid in response to at least the varying flow rate signal.

BRIEF DESCRIPTION OF THE DRAWINGS

The foregoing summary as well as the following detailed description of the preferred embodiment of the invention, will be better understood when read in conjunction with the appended drawings. For the purpose of the illustrating the invention, there is shown in the drawings an embodiment which is presently preferred. It is understood, however, that the invention is not limited to the precise arrangements and instrumentalities shown. In the drawings:

FIG. 1 depicts diagrammatically, the components of a preferred embodiment, automatic calorimeter of the invention;

FIG. 1A is an expanded view of area A of FIG 1; and

FIG. 2 depicts diagrammatically, a sample plot of instantaneous heat flow rate values for an exemplary chemical reaction and for a subsequent calibration heat cycle of the calorimeter of FIG. 1.

DETAILED DESCRIPTION OF THE PREFERRED EMBODIMENT

FIG. 1 depicts diagrammatically a preferred embodiment bench scale calorimeter, denoted generally by the reference numeral 10, for the determining heat of reaction of and thermally controlling a chemically reacting mass. The calorimeter 10 includes a conventional reaction vessel 12, preferably a double glass walled, insulated container, as is shown in FIG. 1A, for containing at least a liquid or solid chemically reacting mass. A fluid circulation system, denoted generally by reference numeral 14, contains a heat transfer fluid (not depicted). The preferred fluid is a silicone oil such as, for example, Rhone Poulenc 47-VR having a rated viscosity of 5 centistokes. The system 14 includes a coil 16 for passing the fluid through the reaction vessel 12. In particular, the coil 16 is positioned within the reaction vessel 12 for intimate exchange of heat between the fluid in the circulation system and a chemically reacting mass contained within the reaction vessel 12. The coil 16 is made of a suitably non-reactive material such as 304 stainless steel. Preferably the coil 16 is removably attached to the remainder of the circulation system 14 by conventional couplings 17 which permit the coil 16 to be removed for cleaning or replacement. The fluid circulation system 14 further includes a circulator 18 which receives through an outlet line 20, the fluid passing through the coil 16 and the reaction vessel 12. The circulator 18 returns that fluid to a predetermined temperature, which is preferably time constant but may vary according to a predetermined time schedule, for recirculating the heat transfer fluid through the coil 16 by an inlet line 22. To accomplish these circulating and temperature adjusting functions, the circulator 18 includes a single, temperature-conditioning reservoir receiving all the heat transfer liquid passing through the coil 16, a refrigeration/heating unit operating in the reservoir and a high efficiency pump. The circulator 18 may be, for example, a Lauda Circulator Model RCS 6 distributed in the United States by Brinkman Instruments.

The calorimeter 10 further includes a fluid flow rate control subsystem, denoted generally by reference numeral 24. According to the invention, the subsystem 24 is at least generally responsive to variations in temperature of the reacting mass within the reaction vessel 12 for varying flow rate of the fluid circulated through the reaction vessel portion of the circulation system. The preferred fluid flow rate control subsystem 24 is, in fact, almost instantaneously responsive to variations in temperature of the reacting mass contained in the reaction vessel 12.

To accomplish its purpose, the fluid flow rate control subsystem 24 includes a valve 26, positioned in the inlet line 22 returning fluid to the coil 16, for varying rate of flow of the heat transfer fluid passing through the reaction vessel portion of the circulation system, i.e. the coil 16. The flow rate control subsystem 24 further includes a valve actuator 28 coupled with the valve 26 for varying the state of valve 26 and thereby varying flow rate of the heat transfer fluid through the coil 16. While any of a variety of valves might be employed, preferably valve 26 is one like a Badger Meter 3-way slide plate valve, for example, having a continuously varying setting for a continuous range of flow rates and three-way so as to proportion the fluid between the inlet line 22 carrying fluid to the coil 16 and a line 30 forming a loop by-passing the coil 16 and returning fluid to the circulator 18. In this way, the load on the pump of the circulator 18 can be held constant. Preferably the actuator 28 is a programmable device such as, for example, a Model 6000-T-MA-MA from Omega Engineering Company of Stamford, Conn., accepting at least one predetermined value representing a pre-set temperature and further responding to a control level voltage signal for providing a proportional response to the difference between the predetermined value and the signal.

Further according to the invention, to calculate the rate of heat transfer between the heat transfer fluid and the reacting mass there is provided a flow rate signal means 32 for generating a first signal related to varying flow rate of the fluid passing through the reaction vessel portion of the fluid circulation system. In the preferred embodiment, the flow rate signal means 32 is a signal generator that includes a flow rate sensing means 33 positioned along the outlet line 20 (or inlet line 22) of the circulation system 14. A suitable flow rate signal generator with sensor is, for exaample, a Microflow Sensor (B-range) with signal converter for 0–5 VDC output and, if desired, a DAD Flow Meter for visual output, all from Cole Parmer of Chicago, Ill. The flow rate signal generated by the signal generator 32 is carried on line 34 to a suitable circuit which is responsive at least to that flow rate signal for generating a heat flow signal generally related to instantaneous rate of heat exchange between the reacting mass and the heat transfer fluid. In the preferred embodiment, such circuitry is provided by a programmable computer 36 such as an Apple Computer Model IIe. Associated with the computer are an operator display screen or CRT 38, a disk drive storage device 40 and a printer 42, each coupled with the computer 36 by lines 39, 41 and 43, respectively.

A first temperature signal means 44 for generating a first temperature signal related to the temperature of the reacting mass within the vessel 12 is provided for controlling the actuator 28. Preferably, the first temperature signal means 44 includes a sensor 45 positioned within the vessel 12 and suitably shielded to be inserted into a chemically reacting mass for sensing to the actual temperature of the reacting mass to generate a first temperature signal passed along line 46 to the valve actuator 28 and along line 47 to the computer 36. A suitable first temperature sensing means 45 is, for example, a Model CPSS-116G-12-FEP, polytetrafluorethylene coated thermocouple, from Omega Engineering, with associated circuitry for compensation and scaling of the thermocouple output to a 0–5 VDC signal range for use by the controller 28 and the computer 36.

Second and third temperature signal generators 48 and 54, respectively, are provided for generating second and third temperature signals related to the temperature of the heat transfer fluid entering and exiting, respectively, the reaction vessel portion of the fluid circulation system. Preferably, the second and third temperature signal generators each include, for example, a thermocouple 50 and 56, respectively, such as a Model CPSS-116U-3-SLE from Omega Engineering, which extends into the coil inlet and outlet lines 22 and 20, respectively, as well as associated circuitry for compensating and scaling the signal generated with each thermocouple 50 and 56 to a 0–5 VDC range for use by the computer 36. The second and third temperature signals, so scaled, are carried to the computer 38 on lines 52 and 58, respectively. The second and third temperature signals are used by the computer 38 with the flow rate signal generated by the flow rate signal generator 32 to generate the heat flow signal.

An auxiliary heat source in the form of an electric heater 60 is provided extending into the interior of the vessel 12 to calibrate the apparatus 10 for determining an absolute heat of reaction. The heater 60 is driven by a suitable electric power source, not depicated. The heater 60 is controlled by the computer 38 through a relay 62 switching the heater power supply on and off. A digital wattmeter 64 is also provided which measures the power being consumed by the heater 60, and outputs a measured wattage value to the computer 38 on line 65 for conversion into calories. A suitable heater 60 is, for example, a Glenn cartridge heater model S3-3210 while a suitable wattmeter is, for example, a Yew model 255510-4004.

The apparatus 10 further includes an electronically controlled stirrer 66 including a variable speed motor 68, drive shaft 70 and removable prop 72, which may be flat or pitched. Rotational speed of the stirrer 66 is measured by suitable, conventional means such as a digital tachometer 74. The tachometer signal is passed to the computer 36 on line 76.

The preferred embodiment calorimeter 10 further includes a reagent dosing subsystem which includes a plurality of reservoirs 78 and 80, the contents of which are fed into the reaction vessel 12 by means of electronically controlled metering pumps 82 and 84 respectively. The pumps 82 and 84 are controlled through the computer 36 by means of relays 88 and 86, respectively. The rate of reagen feed from each of the reservoirs 78 and 80 is determined by positioning the reservoirs on electronic balances 94 and 96, respectively. As indicated, the balances 94 and 96 are coupled directly to the computer 36 by lines 95 and 97, respectively, for display and control of the reagent feed subsystem. Suitable balances are, for example, model PE2000 from Metler Instrument AG; suitable reagent pumps are, for example, Model GR 7133-30 electronic metering pumps from Cole Parmer; and suitable relays are, for example, Model SSR-240V10 solid state relays from Omega Engineering.

Heat flow rate between the reacting mass and heat transfer fluid is determined by the formula:

$$q_r = F(T_o - T_i)K \qquad (1)$$

where $q_r$ = heat flow rate between heat transfer fluid and reacting mass;
F = heat transfer fluid flow rate;
T = temperature of heat transfer fluid exiting the coil;
T = temperature of heat transfer fluid entering the coil; and
K = calibration factor.

The calibration factor K is related to the specific heat of the heat transfer fluid and is determined by activating the heater 60 immersed in the reaction mass. The energy evolved from the heater 60 is measured by the digital wattmeter 64, the output of which is relayed to the computer 36 on line 65. The response of the system to this measured heat load yields the calibration factor K. The preferred embodiment calorimeter has been designed to measure and store values from each temperature signal and the flow rate signal at the rate of 30 data points per minute by means of a multiplexer and analog to digital converter such as, for example, the Adalab add-on package with AI13 high speed option and multiplexer from Interactive Microware, State College, Pa., receiving these various signals at the computer 36. These measured values are stored, together with the instantaneous heat flow signal values generated according to formula (1), for subsequent retrieval to calibrate the instantaneous heat flow data and calculate total heat of reaction.

During the course of an experiment, all computer inputs and the estimated heat flow values are passed by signal on line 39 to operator display screen 38. The values are periodically refreshed such as at two seconds intervals. After each reaction run, the data collected are processed and may be stored on the storage medium of the disk drive 40 and printed through the printer 42, if hard copy is desired.

FIG. 2 illustrates the results of an isothermal batch reaction of an exothermic nature. Instantaneous heat flow values 100, calculated every two seconds according to the formula (1) are recorded. The time varying mean of the data values 100 is represented by a solid curve 102. Also included is a calibration curve 104.

The curve 104 was generated subsequent to the chemical reaction from data 100 derived by operation of the heater 60. Calibration after reaction enables the use of the entire reacted mass as the calibration sample. Thus, the system is configured in essentially the same way (i.e. essentially the same total volume) in which it was configured during the reaction. Alternatively, one or more components, which are not spontaneously reactive, can be fed into the reaction vessel and used as the calibration sample if a calibration run is desired before the reaction. However, typically in such cases, the volume of the calibration sample will be less than that of the reacting mass.

Integration of the calibration curve 104 will yield the calibration factor K. Factor K equals the measured heat (wattmeter measurement) divided by the integral of the calibration curve 104. The factor K can then be applied to the integral of the reaction curve 102 to determine the absolute heat of reaction.

The system is normally operated to maintain the reaction mass at a constant temperature determined by the set point of the valve actuator 28, which functions as the temperature controller. Any deviation from the set point caused by heat liberated or absorbed by the reacting mass is relayed to the actuator 28 through the first temperature thermocouple 45 causing the actuator 28 to adjust the setting three-way control valve 26 to permit the proper amount of heat transfer fluid to be sent to the coil 16 to control the temperature of the reacting mass.

For bench scale operation, the reaction vessel is conveniently sized at about five liters or less in capacity, suggestibly about two liters in capacity for convenience. A two-liter capacity enables a single circulator 18 of the type previously identified to be employed providing a temperature operating range of −30 degrees to 120 degrees Centigrade. The aforesaid circulator 18 has a capacity of approximately 6 liters and is able to circulate the heat transfer fluid at a maximum rate of about 2 liters per minute.

It has been found that reactions in a two-liter capacity vessel are easily controlled with about 100 square inches (about 645 square centimeters) of coil surface area. To provide such a surface area, the tubing of the coil 16 can be, for example, about 0.375 inches (9.5 mm) in outer diameter, coiled in loops about 3.75 inches (95 mm) in outer diameter, one loop contacting the next, to a height of about 3.5 inches (about 90 mm). A coil with an equivalent number of loops, spaced slightly apart from one another to provide a greater coil height, such as about 4.25 inches (about 110 mm), might alternatively be employed for ease of coil cleaning. It is believed that reaction control can be effectively maintained and heat of reaction still accurately measured with a coil surface area to reaction vessel capacity ratio as little as one-half the ratio indicated above, i.e. with a ratio as low as about 25 square inches (about 160 square centimeters) of coil surface area per liter of reaction vessel capacity.

Preferably, the set point temperature of the actuator 28 and the temperature of the reservoir of the circulator 18 are selected to yield a flow rate of the heat transfer fluid so as to maintain a discernible difference between fluid inlet and outlet temperatures. In particular, a temperature difference of at least six degrees Centigrade or more between the heat transfer fluid entering and exiting the coil 16 is preferred to minimize systematic errors occurring in the normal operation of the thermocouples 50 and 56.

The computer 36 can be used to control the feeding of predetermined quantities of each reagent into the vessel 12 by suitable cycling of the solid state relays 86 and 88. As a precaution against runaway reactions, any potentially dangerous temperature deviation of the reaction mass can be used to cause the feed pump relays 86, 88 and the heater relay 62 to be cycled so as to terminate reagent feed and/or heating until the reaction is once again under control. Conveniently, this function can be provided by programming the computer to compare the difference between the reaction temperature and a predetermined temperature or schedule of time varying temperatures against some maximum temperature difference value (or to compare the reaction temperature to an absolute maximum or minimum temperature) and responding if the maximum temperature difference (or the pertinent maximum or minimum temperature) is exceeded.

While a preferred embodiment of the invention has been disclosed, variations will occur to those of ordinary skill in the art. For example, alternatively and less desirably, a signal indicating flow rate may be generated indirectly by calibration of the reaction temperature output signal or a signal generated by the actuator 28 to actual fluid flow rate and used. Also, rather than actually measuring the temperature of the heat transfer fluid being passed into the coil 16, a predetermined value may be entered into the computer's storage, corresponding either to the temperature value preset into the circulator 18 or a measured value of fluid temperature at the reaction vessel corresponding to that set point temperature of the circulator. That value, rather than actual measured input temperature, could also be used to calculate heat transfer rate.

Alternatively, and also less desirably in terms of response time, the actuator 28 may be controlled by the fluid outlet temperature signal. It may even be controlled in some instances by a signal generator predicting a generally known temperature profile for a reaction.

In addition, while a programmable computer is preferred, generation of the instantaneous heat transfer rate signal and determination of the heat of reaction can alternatively be accomplished by firmware or by hard-wired digital and/or analog circuitry.

From the foregoing description, it can be seen that the present invention provides a self-contained, automatic calorimeter with a variable flow rate, heat transfer fluid circulation system for accurate heat transfer measurement and rapid reaction response. In particular, the device 10 has proved invaluable in the control of peroxidation reactions. These reactions evolve a sharp initial charge of heat energy which can result in reaction runaway if not carefully controlled. Also, the accurate, rapid control of heat provided by the subject system is important in achieving uniform yield and product quality.

It will be recognized by those skilled in the art that changes in addition to those already mentioned could be made to the above-described embodiment in the invention, without departing from the broad inventive concepts thereof. It is understood, therefore, that this invention is not limited to the particular embodiment and variations thereto disclosed, but is intended to cover any modification which is within the scope and spirit of the invention, as defined by the appended claims.

We claim:

1. A calorimeter for determining heat of reaction of a chemically reacting mass comprising:
   reaction vessel means for containing the chemically reacting mass;
   a fluid circulation system containing a heat transfer fluid, a portion of the system passing the fluid through the reaction vessel means for exchanging heat between the fluid and the reacting mass;
   flow rate control means at least generally responsive to variations in temperature of the reacting mass for varying flow rate of the fluid circulated through the reaction vessel portion of the circulation system;

flow rate signal means for generating a signal related to varying flow rate of the fluid passing through the reaction vessel portion of the fluid circulation system; and circuit means responsive at least to the flow rate signal for generating a heat flow signal generally related to instantaneous rate of heat exchange between the reacting mass and the fluid.

2. The calorimeter of claim 1 wherein the flow rate signal means comprises flow sensing means for sensing varying flow rate of the fluid passing through the reaction vessel portion of the circulation system.

3. The calorimeter of claim 1 wherein the flow rate control means comprises a valve having a continuously variable setting.

4. The calorimeter of claim 1 wherein the flow rate control means comprises a three-way valve.

5. The calorimeter of claim 1 wherein the reaction vessel portion of the fluid circulation system comprises a coil removably coupled with a remaining portion of the circulation system, the coil being positioned within the reaction vessel means for contacting the reacting mass.

6. The calorimeter of claim 1 further comprising:
a plurality of pumps coupled with the reaction vessel means for feeding any of a plurality of reagents into the reaction vessel means; and
circuit means at least generally responsive to temperature of the reacting mass for deactivating the pumps.

7. The calorimeter of claim 1 wherein the flow rate control means comprises:
first temperature signal means for generating a first temperature signal generally proportional to temperature of the reacting mass;
valve means in the fluid circulation system for variably controlling flow rate of the fluid through the reaction vessel portion of the circulation system; and
valve actuator means coupled with the valve means and responsive to the first temperature signal means for varying the state of the valve means to vary flow rate of the fluid through the reaction vessel portion of the system in response to the reacting mass temperature.

8. The calorimeter of claim 7 wherein the circulation system includes a loop from the valve means by-passing the reaction vessel means portion of the circulation system and wherein the valve means comprises a three-way valve proportioning flow of the fluid between the reaction vessel means portion of the circulation system and the loop.

9. The calorimeter of claim 8 wherein the first temperature signal means comprises temperature sensing means positioned within the reaction vessel means to contact the reacting mass.

10. The calorimeter of claim 9 wherein the fluid circulation system further comprises means for adjusting the temperature of all fluid fed into the reaction vessel means portion of the system to a predetermined temperature.

11. The calorimeter of claim 10 wherein the means for adjusting the temperature is one reservoir receiving all of the fluid passing through the reaction vessel means portion of the circulation system and temperature conditioning means for adjusting the temperature of the fluid in the one reservoir to the predetermined temperature.

12. The calorimeter of claim 9 wherein the reaction vessel means portion of the fluid circulation system comprises a coil removably coupled with the remainder of the circulation system.

13. The calorimeter of claim 12 wherein the reaction vessel means comprises an insulated, transparent glass container about five liters or less in capacity receiving the coil.

14. The calorimeter of claim 9 further comprising:
a plurality of pumps coupled with the reaction vessel means for feeding any of a plurality of reagents into the reaction vessel means; and
circuit means for controlling the operation of the plurality of pumps and responsive to the temperature sensing means for deactivating the pumps when temperature sensed within the reaction vessel means exceeds a predetermined value.

15. A method for determining the heat of reaction of a reacting mass utilizing a reaction vessel and a heat transfer fluid comprising the generally simultaneous steps of:
chemically reacting the mass within the reaction vessel;
circulating the fluid through a fluid circulation system, a portion of the system passing the fluid through the reaction vessel for exchanging heat between the fluid and the reacting mass;
varying flow rate of the fluid passing through the reaction vessel portion of the circulation system at least generally in response to variations in temperature of the reacting mass;
generating a signal related to varying flow rate of the fluid passing through the reaction vessel portion of the circulation system; and
generating a heat flow signal generally related to instantaneous rate of heat exchange between the reacting mass and the fluid in response to at least the varying flow rate signal.

16. The method of claim 15 wherein the varying step comprises:
sensing temperature of the reacting mass; and
varying the state of a valve controlling flow rate of the fluid through the reaction vessel portion of the circulation system in response to the sensed reacting mass temperature.

17. The method of claim 16 wherein the valve state varying step further comprises proportioning with the valve, a continuous flow of the fluid between the reaction vessel portion of the circulation system and a loop by-passing the reaction vessel portion of the circulation system.

18. The method of claim 15 further comprising, at least generally simultaneously with the circulating and varying steps, the step of limiting the flow rate of fluid through the reaction vessel portion of the system to maintain a temperature difference of at least several degrees Centigrade between the fluid entering and the fluid leaving the reaction vessel portion of the system.

19. the method of claim 18 further comprising the steps of measuring the temperature of the fluid entering and measuring the temperature of the fluid exiting the reaction vessel portion of the system and wherein the second generating step further comprises generating the heat flow signal also in response to at least the steps of measuring the temperature of the fluid entering and measuring the temperature of the fluid exiting the reaction vessel portion of the system.

20. The method of claim 15 wherein the fluid circulation system is essentially closed and further comprising the steps of adjusting the temperature of all fluid passing through the reaction vessel means portion of the system to a time-constant, predetermined temperature for recirculation through the reaction vessel portion of the system; and recirculating the fluid at the time-constant, predetermined temperature into the reaction vessel portion of the circulation system.

* * * * *